(12) United States Patent
Grossman et al.

(10) Patent No.: US 7,973,919 B2
(45) Date of Patent: Jul. 5, 2011

(54) HIGH RESOLUTION WAFER INSPECTION SYSTEM

(75) Inventors: Dan Grossman, Herzelia (IL); Moshe Langer, Nes-Ziona (IL); Roman Kris, Jerusalem (IL); Silviu Reinhorn, Mevaseret-Zion (IL); Ron Naftali, Shoham (IL); Haim Feldman, Nof-Ayalon (IL)

(73) Assignee: Applied Materials Israel, Ltd., Rehovot (IL)

( * ) Notice: Subject to any disclaimer, the term of this patent is extended or adjusted under 35 U.S.C. 154(b) by 0 days.

(21) Appl. No.: 12/752,995

(22) Filed: Apr. 1, 2010

(65) Prior Publication Data

US 2010/0188658 A1    Jul. 29, 2010

Related U.S. Application Data

(62) Division of application No. 11/952,010, filed on Dec. 6, 2007, now Pat. No. 7,714,999.

(60) Provisional application No. 60/868,791, filed on Dec. 6, 2006, provisional application No. 60/868,817, filed on Dec. 6, 2006, provisional application No. 60/868,863, filed on Dec. 6, 2006, provisional application No. 60/868,909, filed on Dec. 6, 2006.

(51) Int. Cl.
*G01N 21/00* (2006.01)
(52) U.S. Cl. .................... 356/237.2; 356/237.1
(58) Field of Classification Search ..... 356/237.1–237.5
See application file for complete search history.

(56) References Cited

U.S. PATENT DOCUMENTS

| 5,814,820 | A | 9/1998 | Dong et al. |
| 6,971,791 | B2 | 12/2005 | Borden et al. |
| 7,009,695 | B2 * | 3/2006 | Some ..................... 356/237.1 |
| 7,068,363 | B2 | 6/2006 | Bevis et al. |
| 7,133,128 | B2 | 11/2006 | Clarysse et al. |
| 7,136,163 | B2 | 11/2006 | Borden et al. |
| 2006/0012791 | A1 | 1/2006 | Reinhorn |

OTHER PUBLICATIONS

U.S. Appl. No. 60/868,791, filed Dec. 6, 2006.
U.S. Appl. No. 60/868,817, filed Dec. 6, 2006.
U.S. Appl. No. 60/868,863, filed Dec. 6, 2006.
U.S. Appl. No. 60/868,909, filed Dec. 6, 2006.

* cited by examiner

*Primary Examiner* — Michael P Stafira
(74) *Attorney, Agent, or Firm* — SNR Denton US LLP

(57) ABSTRACT

A method for inspecting a region, including irradiating the region via an optical system with a pump beam at a pump wavelength. A probe beam at a probe wavelength irradiates the region so as to generate returning probe beam radiation from the region. The beams are scanned across the region at a scan rate. A detector receives the returning probe radiation, and forms an image of the region that corresponds to a resolution better than pump and probe Abbe limits of the optical system. Roles of the pump and probe beams may be alternated, and a modulation frequency of the pump beam may be changed, to produce more information. Information extracted from the probe signal can also differentiate between different materials on the region.

4 Claims, 8 Drawing Sheets

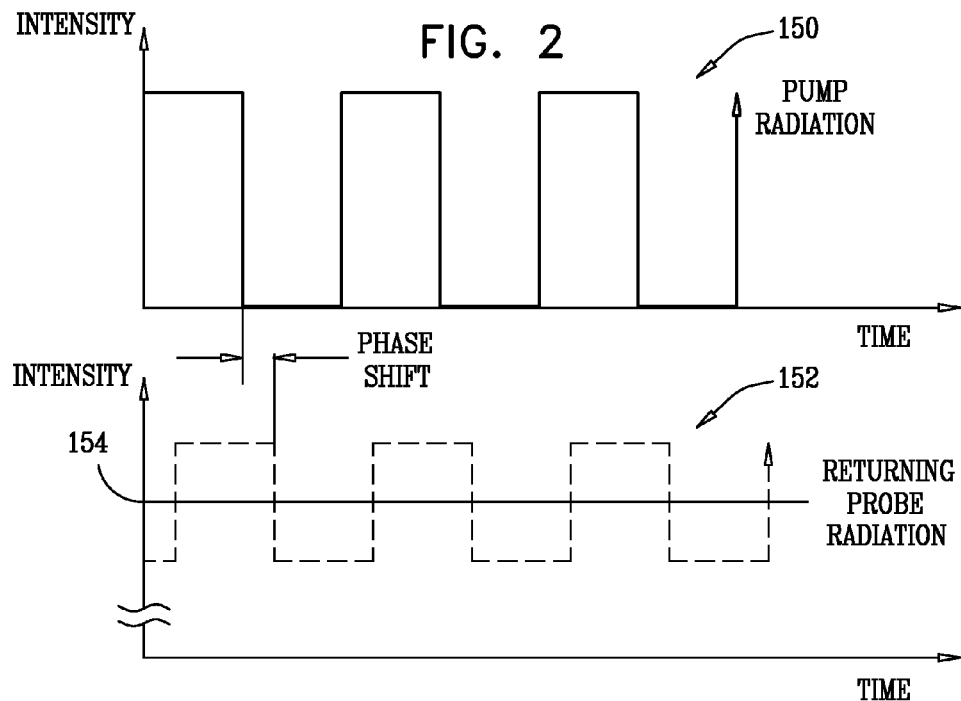
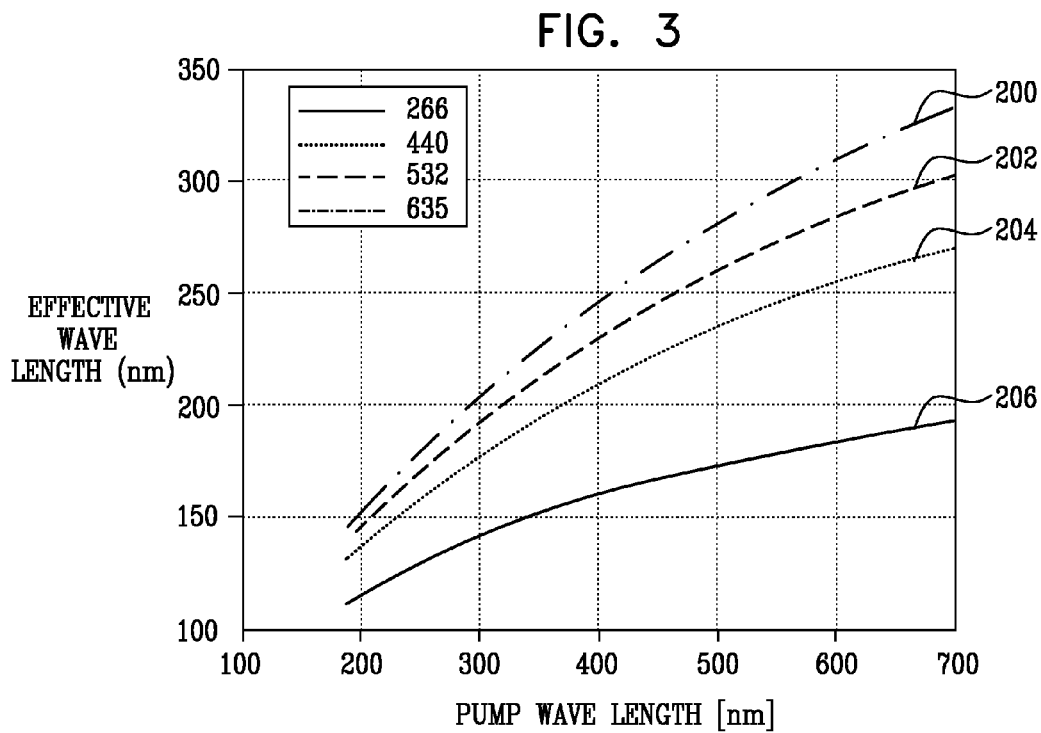

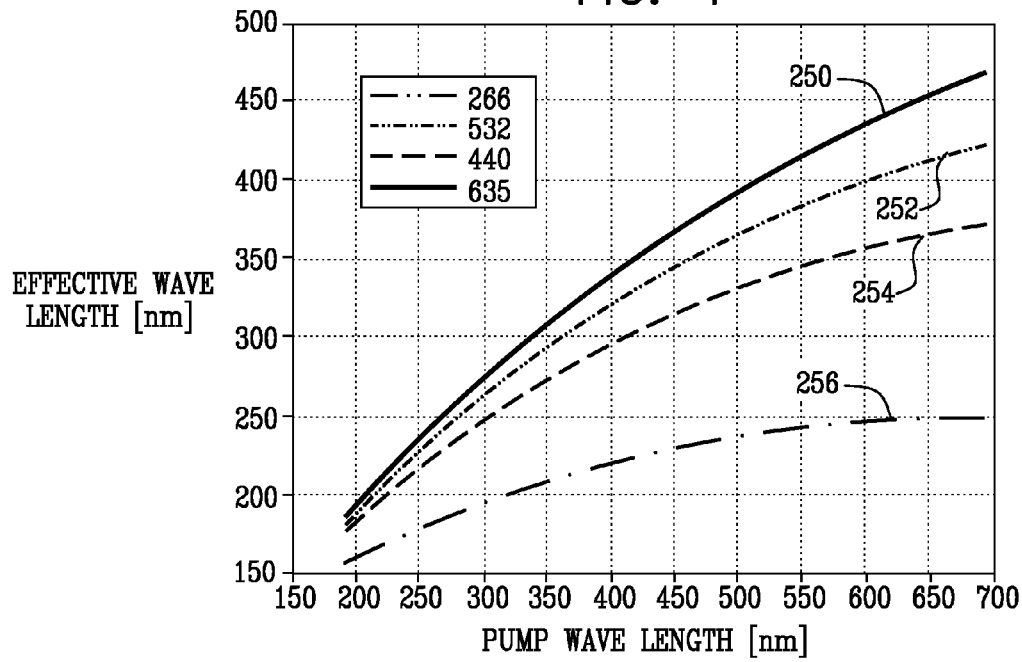
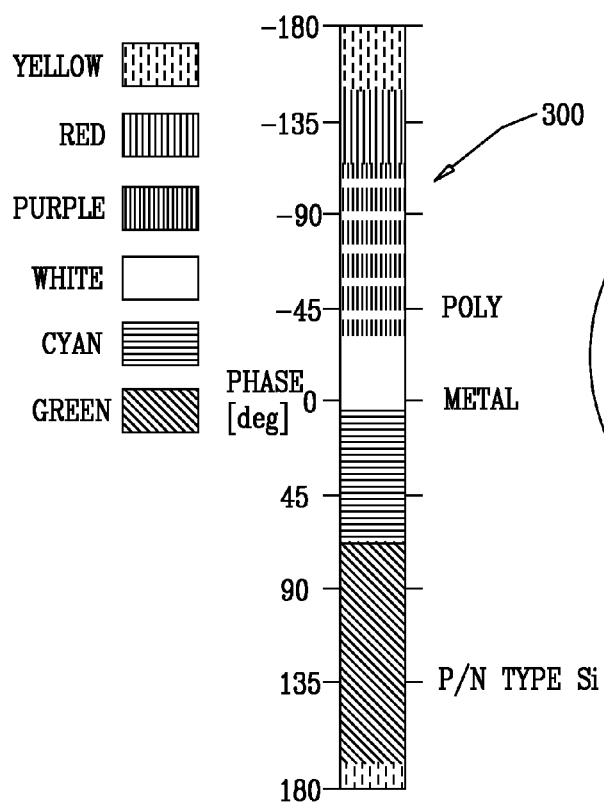
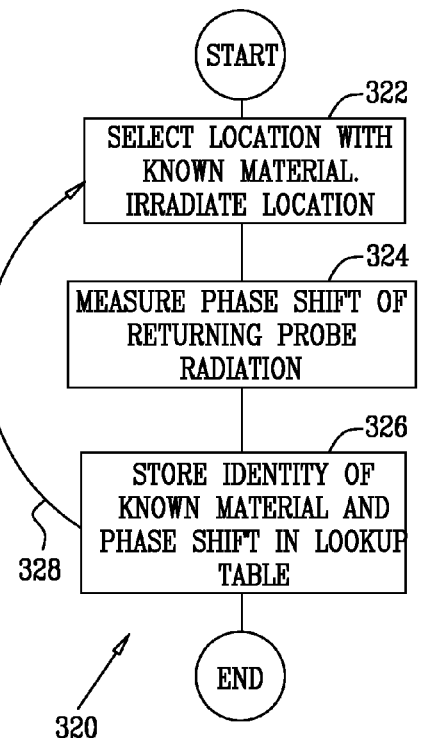

HIGH RESOLUTION WAFER INSPECTION SYSTEM

CROSS-REFERENCE TO RELATED APPLICATIONS

This application is a Divisional of U.S. application Ser. No. 11/952,010 filed 6 Dec. 2007 now U.S. Pat. No. 7,714,999 which claims the benefit of U.S. Provisional Patent Applications 60/868,791, 60/868,817, 60/868,863, and 60/868,909, filed 6 Dec. 2006, which are incorporated herein by reference.

FIELD OF THE INVENTION

The present invention relates generally to inspection systems, and specifically to wafer inspection systems operating at a high resolution.

BACKGROUND OF THE INVENTION

Inspection of wafers, both for defects in wafer features and to confirm that the features conform to specified parameters, is an integral part of the wafer fabrication process. One of the methods known in the art for performing such an inspection uses an opto-thermal pump/probe technique. In this technique a first optical source (the pump) heats a location of the wafer, and a second optical source (the probe) investigates the effect of the heating to determine a property of the location, such as its resistance. U.S. Pat. No. 6,971,791, to Borden et al., whose disclosure is incorporated herein by reference, describes a method for identifying defects in a conductive structure of a wafer. The method is based on measurements of the heat transfer through the conductive structure.

U.S. Pat. No. 7,136,163, to Borden et al., whose disclosure is incorporated herein by reference, describes evaluation of a semiconductor wafer having two regions with different dopant concentration profiles. The evaluation performs measurements indicative of a difference in reflectivity between the regions.

U.S. Pat. No. 7,133,128, to Clarysse, et al., whose disclosure is incorporated herein by reference, describes determining the dopant profile of doped regions in a semiconductor substrate by using a pump laser to create excess carriers in the semiconductor substrate.

SUMMARY OF THE INVENTION

In an embodiment of the present invention, an inspection apparatus includes a pump beam generator, typically comprising a first laser, which generates radiation at a pump wavelength and outputs the radiation as a pump beam. The apparatus includes a probe beam generator, typically comprising a second laser, which generates radiation at a probe wavelength and outputs the radiation as a probe beam. An optical system focuses the pump beam and the probe beam to a region of a substrate, typically a semiconductor substrate, so as to irradiate the region. The optical system also scans the two beams across the region at a scan rate. The pump beam generates a level of excess carriers in the region, and the intensity of returning probe beam radiation from the region is a function of the level.

The optical system conveys the returning probe beam radiation to a detector, which forms an image of the region from the returning radiation. The resolution of the image is better than the Abbe limit of the optical system at either the pump wavelength or the probe wavelength and the detector is sampled in a sample time, which, combined with the scan rate, enables the detector to form the image at an image pixel size corresponding to the better resolution.

Typically, the pump beam is modulated, and the returning probe beam modulates in response to the pump beam modulation. The detector is configured to detect the modulated returning probe beam, thus improving the signal to noise ratio of the image. In some embodiments a phase shift between the returning probe beam and the pump beam is measured. The phase shift may be correlated with a feature material on the substrate, and used to identify the feature material composition. In some embodiments more than one type of feature is present in the irradiated region, and the different types of features may generate different phase shifts. In this case the different features may be identified in the image produced, typically by using different colors in the image for the different types.

In an alternative embodiment of the present invention, a metal is coupled to the substrate, and the pump and probe beams irradiate a region including the metal. The metal is detected from the thermal response of the metal, which typically is characteristic of the metal composition, the shape of the metal, and a pump modulation frequency. The modulation frequency is selected, in response to the thermal response, so as to generate an image of the metal at the higher resolution described above.

In some embodiments, an effective wavelength for the higher resolution is given by the equation:

$$\frac{1}{\lambda_{\it{eff}}} = \frac{1}{\lambda_{pump}} + \frac{1}{\lambda_{probe}}$$

where $\lambda_{\it{eff}}$ is the effective wavelength, $\lambda_{pump}$ is the pump wavelength, and $\lambda_{probe}$ is the probe wavelength.

Alternatively, the effective wavelength for the higher resolution is given by the equation:

$$\frac{1}{\lambda_{\it{eff}}^2} = \frac{1}{\lambda_{pump}^2} + \frac{1}{\lambda_{probe}^2}$$

In some embodiments, the modulation frequency may be varied. The variation may enable a depth below the surface of the substrate to be chosen at which inspection is to be performed. Alternatively, if the region inspected comprises a metal, the variation may enable a thermal capacity of the metal to be measured.

In some embodiments, the roles of the first and second lasers may be switched, so that the inspection apparatus is able to function in two modes. Operation in the first mode is substantially as described above. In the second mode, the second laser operates as the pump laser and is modulated, whereas the first laser is unmodulated and operates as the probe laser. The optical system is typically configured so that the optical properties of the paths followed by both beams, and the detection systems for both beams, are substantially similar. Returning probe beam radiation from both modes may be compared, and generates more information of the irradiated region than either mode alone.

The present invention will be more fully understood from the following detailed description of the embodiments thereof, taken, together with the drawings, a brief description of which follows.

BRIEF DESCRIPTION OF THE DRAWINGS

FIG. 2 shows schematic intensity vs. time graphs for the apparatus, according to an embodiment of the present invention;

FIG. 3 shows schematic graphs of effective wave length vs. pump wave length, according to an embodiment of the present invention;

FIG. 4 shows schematic graphs of effective wave length vs. pump wave length, according to a disclosed embodiment of the present invention;

FIG. 5A is a chart used to display images, and FIG. 5B is a flowchart illustrating how the chart is generated, according to an embodiment of the present invention;

DETAILED DESCRIPTION OF EMBODIMENTS

Figure 1A:
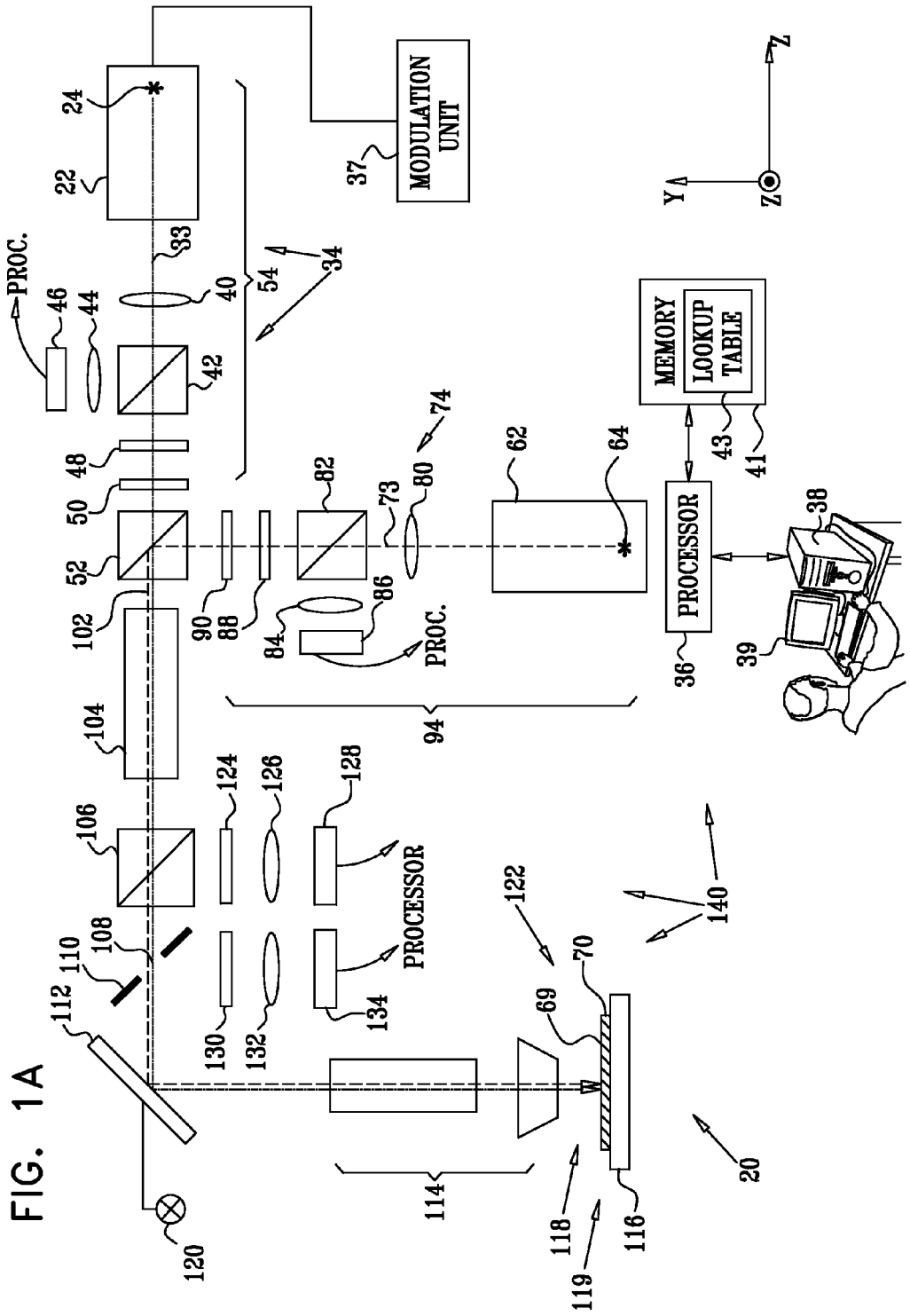
FIG. 1A is a schematic diagram illustrating a wafer inspection apparatus, according to an embodiment of the present invention.

Reference is now made to FIG. 1A, which is a schematic diagram illustrating a wafer inspection apparatus 20, according to an embodiment of the present invention. Apparatus 20 is used to inspect features on and/or close to a surface of an object 70, herein by way of example assumed to be a wafer produced in a semiconductor fabrication process, and the description hereinbelow is directed to such a use. However, it will be appreciated that apparatus 20 may be used to inspect features on and/or close to a surface of materials produced in other processes. Apparatus 20 is typically incorporated into an inspection tool wherein wafer 70 is being inspected, although herein the inspection tool and elements associated with the inspection tool are not shown for reasons of clarity.

As is described in more detail below, the inspection process used by apparatus 20 is based on irradiating a top surface 69 of wafer 70 with radiation, herein termed pump radiation, that interacts with the wafer. Hereinbelow the pump radiation is assumed to be intensity modulated at a modulation frequency. Typically, surface 69 comprises a plurality of entities having different characteristics. For example, the surface may be composed of metals such as copper, aluminum, gold, or titanium, semiconductors such as monocrystalline silicon, polycrystalline silicon, or silicon which has been doped with different elements and/or at different concentrations, and dielectrics such as silicon dioxide or silicon nitride. The surface is formed according to generally standard procedures in a fabrication facility, so that an image of the surface may be correlated with an expected arrangement of the different entities.

The wafer is inspected by irradiating the wafer with probe radiation, and receiving and analyzing the probe radiation that returns from the wafer. The returning probe radiation comprises radiation which is modulated at the modulation frequency. The modulated radiation is extracted from the returning radiation, typically using a lock-in amplifier detection system, although any other convenient system may be used. The analysis of the extracted radiation may then be performed by a processor 36 using software stored in a memory 41. The processor and the software also operate apparatus 20 and its component elements. A user interface 38 coupled to the processor allows an operator of apparatus 20 to control the operation of the processor, and to see the results.

User interface 38 comprises a color monitor 39, which displays the results generated by the processor to the operator. As is described in more detail below, the results may be displayed on display 39 in differing colors, the colors being selected to present different aspects of the results, using a lookup table 43 which is stored in memory 41. The lookup table is described in more detail with reference to FIG. 5B below. Presenting the results in different colors enhances the ability of the operator to register significant aspects of the processed image, although it will be appreciated that any other method of viewing the information is plausible.

Some elements of apparatus 20 are assumed, by way of example, to be positioned relative to a set of orthogonal x, y, z coordinate axes, where the x and y axes are in the plane of the paper and the z axis is out of the plane of the paper. For example, surface 69 is assumed to lie in an xz plane. It will be appreciated, however, that the assumption that some elements of apparatus 20 are positioned relative to a particular axis or set of axes is purely for the purposes of clarity in the following description, and that the elements may be positioned in any convenient orientation.

Apparatus 20 comprises a first source 22, typically comprising a diode laser 24, which transmits a first beam 34. En an embodiment of the present invention, the wavelength of the first source is selected to be in a range 400 nm-550 nm. However, it will be appreciated that the wavelength may be selected to have any other beneficial value. Unless indicated otherwise below, first source 22, first beam 34, and the wavelength of the first source may also be referred to respectively as pump source 22, pump beam 34, and the first wavelength or the pump wavelength.

The output from source 22 is intensity modulated at a frequency f. Typically the modulation of beam 34 may be accomplished by a modulation unit 37 that is driven by processor 36, which determines the frequency f and a percentage p by which the intensity is modulated. Typically f is of the order of 1 MHz, and the modulation amplitude p is set to be of the order of 100%, corresponding to unit 37 operating source 22 in an on-off mode. Hereinbelow, except as otherwise stated, processor 36 is assumed to maintain frequency f at a substantially constant value.

Beam 34 passes via optics 40 through a first beam splitter 42, which diverts a portion of the energy of the beam via a focusing lens 44 to a pump reference detector 46. Processor 36 receives respective signals generated by the detector, and may use the signals for normalization of received image signals. Beam 34 passes through a half-wave plate 48 and optionally a quarter-wave plate 50, acting to control the beam polarization, to a beam combiner 52. Combiner 52 is configured to transmit the wavelength of beam 34, and to reflect the wavelength of beams from a probe beam generator 94, described below. The path followed by beam 34 is shown schematically as a line 33.

The components generating beam 34, i.e., those numbered 22, 24, 40, 42, 44, 46, 48, and 50, comprise a pump beam generator 54 which generates pump beam 34.

Probe beam generator 94 comprises a second source 62, comprising a laser 64, typically a diode laser, which projects a second beam 74. The laser is selected to generate a wavelength, which, in one embodiment of the present invention, is selected to be in a range 600 nm-800 nm. The path followed by beam 74 is shown schematically as a broken line 73. Unless indicated otherwise below, second source 62, second beam 74, and the wavelength of the second source may be referred to respectively as probe source 62, probe beam 74, and the second wavelength or the probe wavelength.

Generator 94 further comprises a collimating lens 80, a beam splitter 82, a focusing lens 84, a probe reference detector 86, a half-wave plate 88, and a quarter-wave plate 90, which are configured in substantially the same relative arrangement and perform substantially the same functions as components 40, 42, 44, 46, 48, and 50 respectively. Thus, generator 94 transmits a parallel probe beam 74 to beam combiner 52. However, unlike pump beam generator 54, processor 36 does not intensity modulate probe beam 74, and may use the signals derived from detector 86 to normalize the reflected signals so as to eliminate probe laser noise. The beams output from combiner 52, comprising parallel beam 34 and parallel beam 74, are herein termed beam pair 102. Typically beam pair 102 comprises coaxial beams, although the pair may be non-coaxial. For the purposes of clarity, the beams are shown as separated in FIG. 1.

Pair 102 traverses a set of relay optics 104, a beam splitter 106, and an aperture 108 in a mirror 110, to a scanning mirror 112 which is configured to scan the pair in two dimensions on surface 69. Optics 104 images the beam pair onto mirror 112; the functions of beam splitter 106 and mirror 110 are described below.

Scanning mirror 112 reflects beam pair 102, via a relay and focusing optical system 114, to top surface 69 of wafer 70. Wafer 70 is mounted and supported on a stage 116, typically a motion stage which is able to alter the position of wafer in the x, y and z directions. Optical system 114 is configured to focus beam pair 102 to a pump spot 118 from the pump beam and to a probe spot 119 from the probe beam, both spots irradiating surface 69. Spots 118 and 119 are generally circular, and are typically configured to be substantially concentric on surface 69. System 114 is typically configured so that a size of spots 118 and 119, the size being measured as a diameter of the spot at the half-power points of the spot, is approximately equal to the Abbe limit of the wavelength generating the spot.

During operation of apparatus 20, scanning mirror 112 scans beam pair 102 so that spots 118 and 119 move over surface 69 at a scan rate that is determined by processor 36. Scanning mirror 112 is operated by a motion stage 120, the mirror and stage 120, together with stage 116, being configured so that spots 118 and 119 may be positioned at substantially any location on surface 69. It will be appreciated that apparatus 20 may comprise other scanning units, known in the art, for scanning the spots over surface 69. For example, mirror 112 may comprise a single plane mirror, and/or a polygonal mirror formed from a number of different plane mirrors. Such mirrors may be mechanically or electro-mechanically scanned. Alternatively or additionally, scanning of the spots may be accomplished using an acousto-optic deflector, or by other means known in the art, such as mechanical movement of stage 116.

In some embodiments of the present invention, pump beam 34 and/or probe beam 74 are linearly polarized. Alternatively or additionally one or more of the beams are circularly or elliptically polarized. The polarizations are produced by the half and quarter wave plates which the beams traverse.

As described above, beam pair 102 generates spots 118 and 119 at the surface 69 of wafer 70, and the beam pair interacts with the surface to generate reflected and/or scattered radiation from the locations on the surface irradiated by the spots. The reflected and/or scattered radiation is hereinbelow referred to as returning radiation, and except where otherwise stated, the returning radiation is assumed by way of example to be from location 122. The elements of apparatus 20 are configured so that optical system 114 collects at least a portion of the returning radiation, and together with mirror 112 directs the collected portion to initially traverse substantially the same path as the incoming beam pair. Thus the collected portion of the returning radiation returns to mirror 110 and beam splitter 106.

The returning radiation comprises, specular and scattered radiation from location 122. The specular radiation, also known as bright field (BF) radiation, passes through aperture 108 to beam splitter 106. Splitter 106 is configured to be substantially transparent to pump beam radiation, and to partially reflect probe beam radiation. Thus, specular probe beam radiation is reflected by splitter 106, via a narrow band transmission filter 124 and focusing optics 126, to an imaging detector 128. Filter 124 typically transmits probe wavelengths and is opaque to pump wavelengths. Signals from detector 128 are transferred to processor 36.

The scattered radiation from location 122, also known as gray field (GF) or dark field (DF) radiation, is reflected by mirror 110, via a narrow band transmission filter 130, which is generally similar to filter 124, and focusing optics 132, to an imaging detector 134. Detector 134 detects scattered probe returning radiation, and signals from the detector are transferred to processor 36.

Typically, detector 128 and detector 134 comprise charge coupled devices (CCDs,) PIN diodes, photodiodes, or photomultiplier tubes. Each detector is also assumed to comprise a respective analog-to-digital converter (ADC), which digitizes the signal formed on the detector, and transfers the digitized signals to processor 36. A sample time of each ADC, taken together with the scan rate of spots 118 and 119 described above, determines the effective pixel size used by apparatus 20. Processor 36 sets the scan rate of the spots, and/or the sample time of the ADC of detectors 128 and 134, to generate a required pixel size. Alternatively, detector 128 and/or detector 134 may comprise an array of sub-detectors.

As stated above, processor 36 controls the adjustments of elements of the apparatus such as mirror 112, and processor 36 is in turn controlled by an operator of apparatus 20 via user interface 38. Processor 36 also receives the output from imaging detectors 128 and 134, and processes the outputs to provide results of the inspection of wafer 70. Detectors 128, 134, and processor 36 act as a receiving unit 140 for apparatus 20 that generates the results. The results may be accessed by the apparatus operator via interface 38.

Figure 1B:
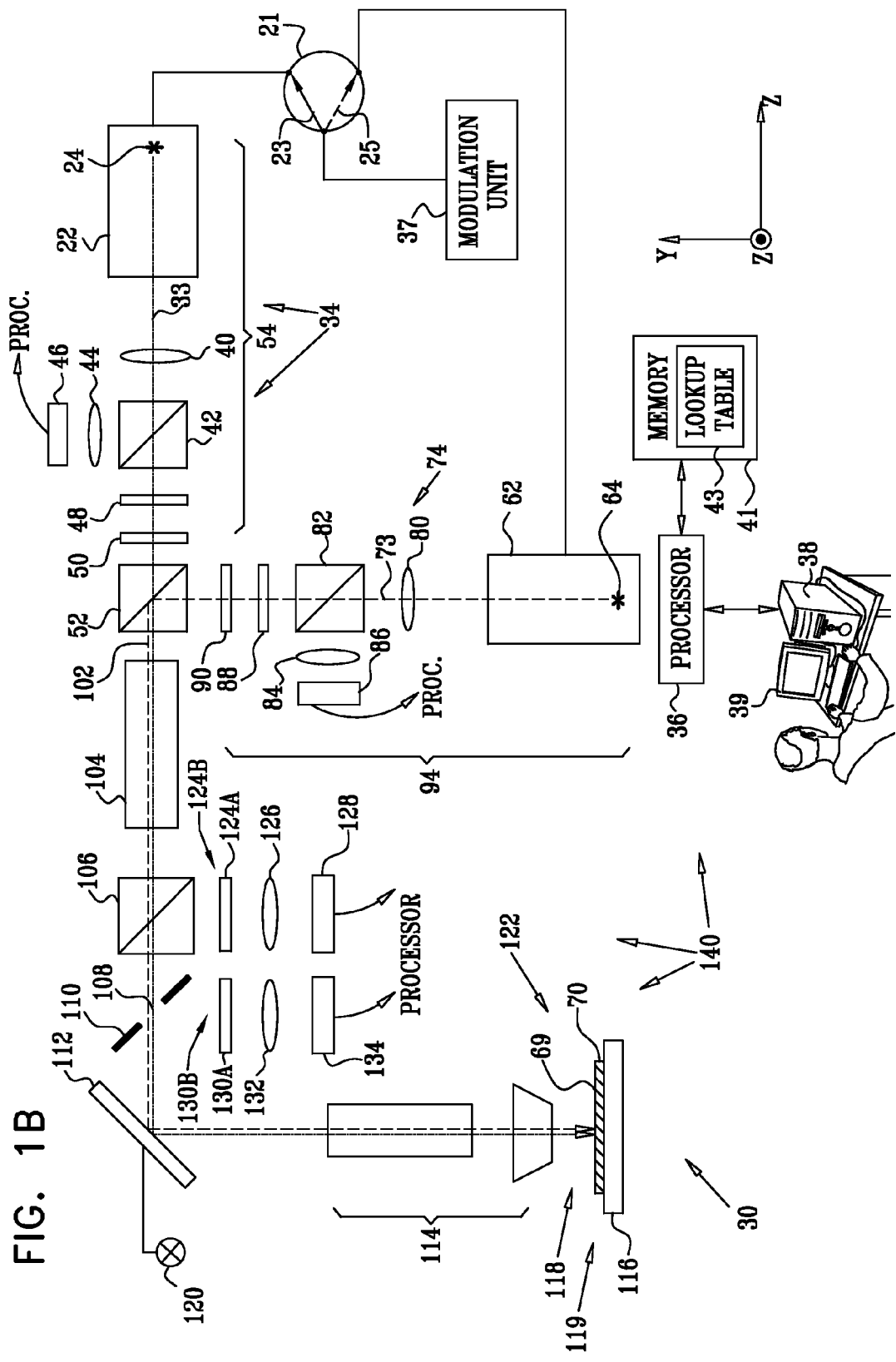
FIG. 1B is a schematic diagram illustrating a wafer inspection apparatus, according to an alternative embodiment of the present invention.

FIG. 1B is a schematic diagram illustrating a wafer inspection apparatus 30, according to an alternative embodiment of the present invention. Apart from the differences described below, the operation of apparatus 30 is generally similar to that of apparatus 20 (FIG. 1A), and elements indicated by the same reference numerals in apparatus 20 and apparatus 30 are generally similar in construction and in operation. Apparatus 30 comprises a switch 21 which may couple the modulation from unit 37 to source 22 or to source 62. Apparatus 30 comprises a first set of narrow band transmission filters 130A and 124A, which are substantially similar to filters 130 and 124, transmitting the second wavelength. Apparatus 30 also comprises a second set of narrow band transmission filters 130B and 124B, which transmit the first wavelength.

Apparatus 30 is configured to operate in two modes, in contrast to apparatus 20 which operates in one mode. In apparatus 30, operation in a first mode is substantially as described above for apparatus 20, wherein modulation unit 37 modulates first source 22, which acts as a pump source. In the first mode second source 62 is not modulated and functions as a probe source. Operation in the first mode is schematically illustrated by a first position 23 of an arm of switch 21 shown in FIG. 1. In the first mode, filters 130A and 124A are positioned in front of detectors 134 and 128, and perform substantially similar functions as filters 130 and 124 of apparatus 20, transmitting at the second wavelength.

In a second mode of operation, the roles of first source 22 and second source 62 are reversed, so that second source 62 acts as a pump source, and first source 22 acts as a probe source. Second source 62 is modulated by unit 37, and first source 22 is unmodulated. Operation in the second mode is schematically illustrated by a second position 25 of the arm of switch 21. In the second mode, filters 130B and 124B are positioned in front of detectors 134 and 128, in place of filters 130A and 124A. Filters 130B and 124B perform substantially similar functions as filters 130A and 124A, except that filters 130B and 124B transmit at the first wavelength, which in the second mode is the wavelength of the probe source.

In the second mode of operation, generator 94 becomes a pump beam generator, and generator 54 becomes a probe beam generator.

In apparatus 30, beams 34 and 74 follow different paths, although some of the elements in the paths are common. Apparatus 30 is typically configured so that the optical parameters of each of the paths match. The optical parameters include, but are not limited to, an overall numerical aperture of each of the paths, and numerical apertures of individual optical elements in the paths.

Apparatus 30 is typically operated by scanning surface 69 in the first and the second mode, and analyzing the returning probe beam signals received in both modes. It will be understood that switching between the two modes may be performed by processor 36, with substantially no change in the architecture of apparatus 30.

The description below, except where indicated otherwise, assumes that apparatus 20 is operative. Those having ordinary skill in the art will be able to apply the description, mutatis mutandis, to the operation of apparatus 30.

FIG. 2 shows schematic intensity vs. time graphs for apparatus 20, according to an embodiment of the present invention. A first graph 150 illustrates the intensity modulated output from pump source 22, as measured by detector 46 (FIG. 1). By way of example, herein the modulation is assumed to be an on-off modulation generating a square wave, with approximately equal times for the on and off periods. However, any other convenient intensity modulation, such as a sine wave modulation, may be applied to the pump source. A lower graph 152 schematically illustrates, on a different intensity scale from that of the pump source, the intensity modulated signal generated at detector 128 and/or detector 134 due to returning probe radiation. Typically, the AC component of the returning probe radiation is of the order of $10^{-3}$ times the DC component of the returning probe radiation.

Pump spot 118 is intensity modulated as a consequence of the intensity modulation of the pump radiation. The modulation of the pump spot causes substantially synchronous changes in characteristics of location 122. The character changes of location 122 modulate the probe radiation irradiating the location, so that the returning probe radiation, illustrated in graph 152, is also modulated in synchronization with the pump radiation. By way of example, the intensity for graph 152 is assumed to comprise the sum of the signals on detectors 128 and 134, and a mean level 154 of the graph is assumed to be the intensity of the returning probe radiation.

However, as shown in graphs 150 and 152, there is typically a phase difference, also herein termed a phase shift, between the pump radiation and the returning probe radiation. The phase shift depends on the characteristics of location 122. For example, if location 122 comprises metal, the phase shift is typically close to zero. If location 122 comprises polycrystalline silicon, the returning probe radiation is typically delayed by approximately 45° compared to the pump radiation. The phase shift values given here are for f of the order of 1 MHz, and typically depend on the value of f, and are also somewhat influenced by the geometry of the feature under inspection. As is explained in more detail below, embodiments of the present invention use the shifts in phase of returning probe radiation to identify different materials on surface 69.

FIG. 3 shows schematic graphs of effective wave length vs. pump wave length, according to an embodiment of the present invention. The resolution of an optical system is a function of an effective wavelength operating in the system, and the resolution may be quantified in terms of an Abbe limit (d), which is a spacing of lines on an object being inspected that can just be resolved by the system. The Abbe limit is equal to about half the diameter of a spot that may be focused onto the object. For a single wavelength system, having an effective numerical aperture $(NA_{eff}) \approx 1$:

$$s \approx \lambda \text{ and } d = \frac{s}{2} \approx \frac{\lambda}{2} \tag{1}$$

where:
s is the diameter of the spot,
λ is the wavelength of the radiation forming the spot, and
d is the Abbe limit.

Equation (1) applies for a system such as apparatus 20 if $NA_{eff} \approx 1$ and if only pump irradiation, or if only probe irradiation, is used. In this case, from equation (1), if surface 69 is irradiated with only pump beam 34, at a wavelength $\lambda_{pump}$=440 nm, the Abbe limit is approximately 220 nm, so that the resolution of the system at this wavelength is approximately 220 nm. If surface 69 is irradiated with only probe beam 74, at a wavelength $\lambda_{probe}$=635 nm, the Abbe limit is approximately 318 nm; so that the resolution in this case is approximately 318 nm.

As described above, surface 69 is irradiated by both the pump and the probe beam simultaneously. The pump radiation from pump source 22 interacts with the material, at location 122, that is irradiated. If location 122 comprises a metal or a dielectric, the main interaction is typically heating of the material. If location 122 comprises a semiconductor, the main interaction is typically excitation of carriers in the material.

The probe radiation returning to detectors 128 and 134 is effectively a multiplication of the point spread function (PSF) of probe spot 119 with the response of the material to the irradiation of the pump spot 118. When provisions are made (by controlling the pump modulation) so that the material reaction to the pump is similar to the PSF of pump spot 118, there is effectively a multiplication of pump and probe spots. The multiplication causes an effective wavelength $\lambda_{eff}$ of images generated by the pump-probe irradiation to be less than the pump wavelength $\lambda_{pump}$, and also to be less than the probe wavelength $\lambda_{probe}$, and a theoretical relationship between $\lambda_{eff}$, $\lambda_{pump}$, and $\lambda_{probe}$ is given by equation (2):

$$\frac{1}{\lambda_{eff}} = \frac{1}{\lambda_{pump}} + \frac{1}{\lambda_{probe}} \quad (2)$$

The derivation of equation (2) will be apparent to persons having ordinary skill in the optical arts. Equation (2) may be rearranged to equation (3):

$$\lambda_{eff} = \frac{\lambda_{probe} \cdot \lambda_{pump}}{(\lambda_{pump} + \lambda_{probe})} \quad (3)$$

Graphs 200, 202, 204, and 206 illustrate the relationship of equations (2) and (3) for four probe wavelengths: 635 nm, 532 nm, 440 nm, and 266 nm. For example, the equations and graph 206 show that for a value of $\lambda_{pump}=440$ nm and $\lambda_{probe}=635$ nm, the effective wavelength $\lambda_{eff}$ of images generated by apparatus 20, if $NA_{eff} \approx 1$, is 260 nm. In this case, equation (1) gives the Abbe limit as approximately 130 nm, so that the resolution of apparatus 20 using both the pump and the probe beams simultaneously is approximately 130 nm. Processor 36 and detectors 134 and 128 are thus advantageously configured so that the respective ADCs of the detectors are sampled at a sample time that generates an image pixel size of approximately 130 nm.

On consideration of the resolutions above, it will be appreciated that the resolution of apparatus 20 operating both the probe and the pump beams simultaneously is better than the resolution of the apparatus operating with only the pump beam or only the probe beam.

FIG. 4 shows schematic graphs of effective wave length vs. pump wave length, according to a disclosed embodiment of the present invention. In the disclosed embodiment described herein, the inventors determined that $NA_{eff} \approx 0.7$. In this case, equation (1) becomes:

$$s \approx \frac{\lambda}{NA_{eff}} \text{ and } d = \frac{s}{2} \approx \frac{\lambda}{2 \cdot NA_{eff}} \quad (4)$$

The inventors have found that for the disclosed embodiment a relationship between $\lambda_{eff}$, $\lambda_{pump}$, and $\lambda_{probe}$ is given by equation (5):

$$\frac{1}{\lambda_{eff}^2} = \frac{1}{\lambda_{pump}^2} + \frac{1}{\lambda_{probe}^2} \quad (5)$$

Equation (5) may be rearranged to equation (6):

$$\lambda_{eff} = \frac{\lambda_{probe} \cdot \lambda_{pump}}{(\lambda_{pump}^2 + \lambda_{probe}^2)^{1/2}} \quad (6)$$

Graphs 250, 252, 254, and 256 illustrate the relationship of equations (5) and (6) for four probe wavelengths: 635 nm, 532 nm, 440 nm, and 266 nm. For example, the equations and graph 256 show that for a value of $\lambda_{pump}=440$ nm and $\lambda_{probe}=635$ nm, the effective wavelength $\lambda_{eff}$ of images generated by apparatus 20 is 362 nm. For the disclosed embodiment, the Abbe limits, from equation (4) are respectively approximately 310 nm, 450 nm, and 260 nm, for the pump beam operating alone, for the probe beam operating alone, and for the pump and probe beams operating simultaneously.

As for the embodiment described above with respect to FIG. 3, the resolution of apparatus 20, for $NA_{eff} \approx 0.7$, for operating both the probe and the pump beams simultaneously is better than the resolution of the apparatus operating with only the pump beam or only the probe beam.

FIG. 5A illustrates a color chart 300 used to display images, and FIG. 5B is a flowchart 320 illustrating how chart 300 is generated, according to an embodiment of the present invention. In FIG. 5A, different shadings represent different colors. Typically there are significantly more colors in chart 300 than are shown in the figure. Chart 300 gives a color that is used on color monitor 39 (FIG. 1) to register the phase differences of returning probe radiation compared with the pump radiation. In an embodiment of the present invention, the phase differences correspond to characteristic differences on surface 69, as described above with reference to FIG. 2.

In some embodiments of the present invention, to generate chart 300, an operator of apparatus 20 performs the steps of flowchart 320. In a first step 322, the operator selects location 122 to have a known material, for example, location 122 may be selected to comprise n-doped silicon. Location 122 is then irradiated by the pump and probe radiations.

In a second step 324 a phase shift of the returning probe radiation, compared with the incident pump radiation, is measured by processor 36 using signals from detector 46, detector 134, and/or detector 128.

In a third step 326, processor 36 stores in memory 41 the phase shift and an identity of the material selected in step 322.

Typically, the operator iterates steps 322, 324, and 326 for different known materials on surface 69, as indicated by a line 328 of the flowchart. After the iterations, flowchart 320 ends, and the different pairs of values of material identity and measured phase difference are stored in lookup table 43.

It will be understood that flowchart 320 is one example of a method for correlating phase shifts of returning probe radiation with a composition or characteristic of the irradiated material. Other methods for generating the correlation of lookup table 43, such as scanning a region of surface 69 having known constituents, will be familiar to those having ordinary skill in the art, and are assumed to be included in the scope of the present invention.

Chart 300 shows the materials polycrystalline silicon (POLY), a metal, and p- and n-type doped silicon, and the respective phase shifts generated by the materials, as recorded in lookup table 43. The differences in phase shift are typically caused by the differences in material, and by the differences in time for an irradiated region to reach a quasi-steady state. Processor 36 assigns colors shown in the chart to the phase shifts, so that lookup table 43 shows equivalences between materials, generated phase shifts, and assigned colors. Table I below shows entries in lookup table 43, corresponding to FIG. 5A.

TABLE I

| Material | Generated Phase Shift | Assigned Color |
| --- | --- | --- |
| Polycrystalline Silicon | −45° | Purple |
| Metal | 0° | White |
| p-doped silicon, n-doped silicon | +135° | Green |

The embodiments described above have described how apparatus 20 generates images differentiating between materials having different characteristics. The description above is by way of example, so that it will be understood that materials having other types of different characteristics may be differentiated. For example, silicon doped with a low level of cobalt may be differentiated from silicon doped with a high level of cobalt because the two types of silicon have different band gaps which generate different levels of excess carriers. The different excess carrier levels may generate different phase shifts in graph 152 (FIG. 2).

Figure 6:
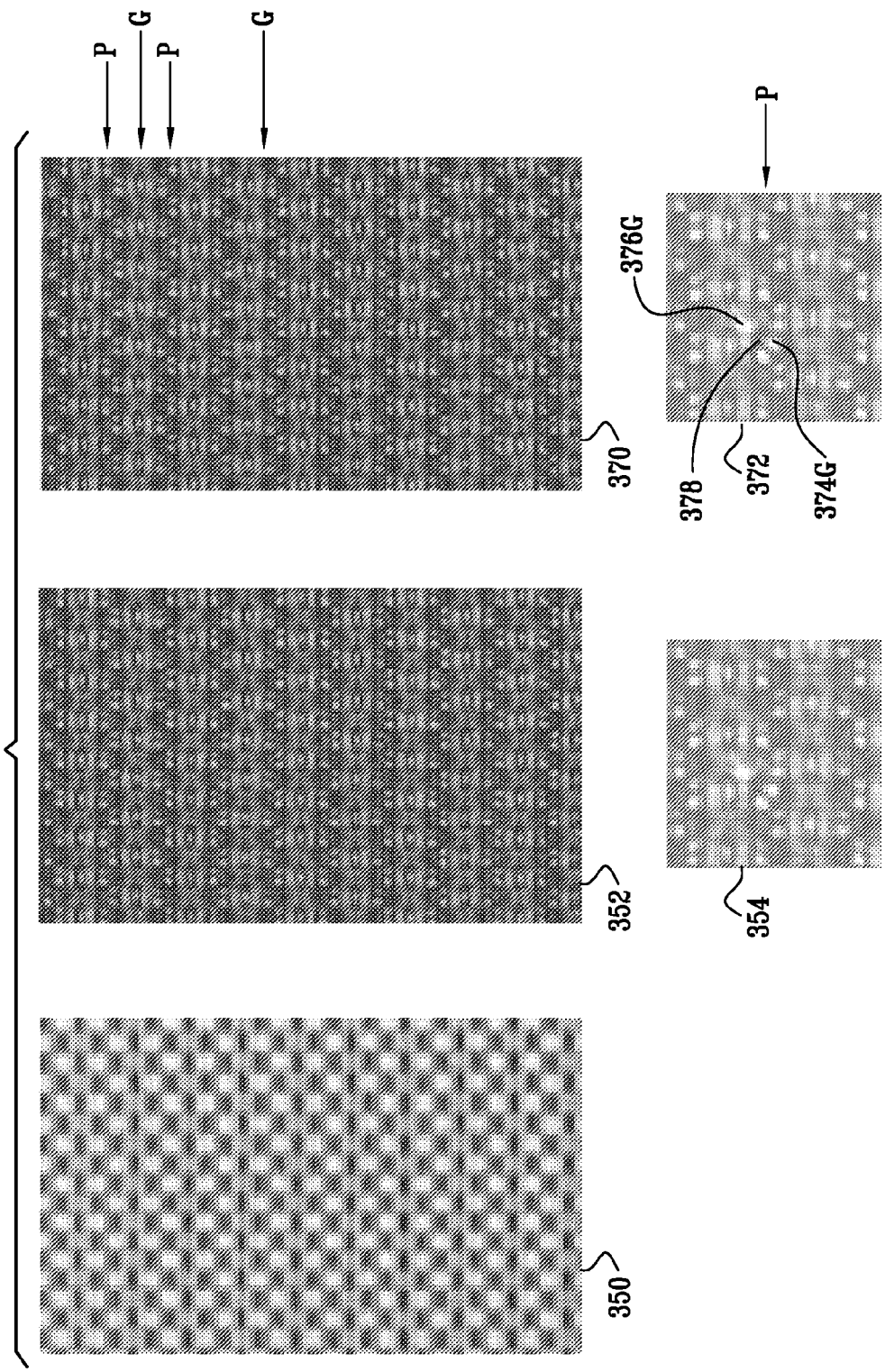
FIG. 6 shows schematic illustrations of a set of images generated by the apparatus of FIG. 1, according to an embodiment of the present invention.

FIG. 6 shows schematic illustrations of a set of images generated by apparatus 20, according to the disclosed embodiment of the present invention described above with reference to FIG. 4. For all the images in FIG. 6, the scan rate of spots 118 and 119, and the sample time of the ADCs of detectors 134 and 128, are set so that a pixel size of the image corresponds with the effective wavelength $\lambda_{eff}$ given by equations (5) and (6). The images are generated with a pump beam having a wavelength $\lambda_{pump}$=440 nm, a probe beam having a wavelength $\lambda_{probe}$=635 nm, and a pixel size of approximately 260 nm, corresponding with the Abbe limit of the disclosed embodiment operating with both the pump and the probe beams. The images are of a region of surface 69 having a repetitive pattern.

A first gray-scale image 350 is produced by detectors 134 and 128 using only probe beam 74. A second gray-scale image 352 is generated using intensities measured by the detectors when both probe beam 74 and pump beam 34 are operative. Comparison of image 350 with image 352 shows that in image 352 there is significantly more detail resolved, illustrating the gain in resolution obtained by the disclosed embodiment.

In a color image 370, phase information from the detectors, corresponding to that described above for FIG. 5A, is incorporated into image 352. By way of example, image 370 has two colors, purple and green, derived from chart 300, applied to the image. In image 370, sections of the image in line with arrows P are purple, and sections of the image in line with arrows G are green. For clarity in image 370, only parts of the image have been labeled with colors P, G. It is assumed that a process generally similar to flowchart 320 has been implemented to generate the chart of Table I. The phase information has been translated into colors according to chart 300 and Table I above, so that purple represents polycrystalline silicon, and green represents p- or n-doped silicon.

Image 370 combines the high image resolution provided by apparatus 20, the phase shift measured by the apparatus, and the application of color to the image. The combination provides an image to an operator of apparatus 20 which has significantly more information than image 350. Furthermore, the application of color to the image provides the information to the operator in an easily assimilated form. It will be appreciated that such a presentation enables an operator of apparatus 20 to quickly and accurately locate the position of a feature, such as a defect, on surface 69, as well as to identify the composition of the feature. Images 354 and 372 exemplify such a defect.

Gray-scale image 354 and color image 372 are of a region of the pattern having a defect. Images 354 and 372 are generated substantially as described above for images 352 and 370 respectively, and for clarity are shown in FIG. 6 as enlarged. In image 372 colors of regions in line with arrow P are purple, and regions labeled with a suffix G are green. Inspection of images 354 and 372 shows that detail of the defect is well resolved. In addition, image 372 shows that defect regions 374G and 376G have the anomalous presence of doped silicon, and that a defect region 378 has the anomalous absence of polycrystalline silicon.

Figure 7A:
FIG. 7A is a schematic diagram of gratings imaged by the apparatus.
Figure 7B:
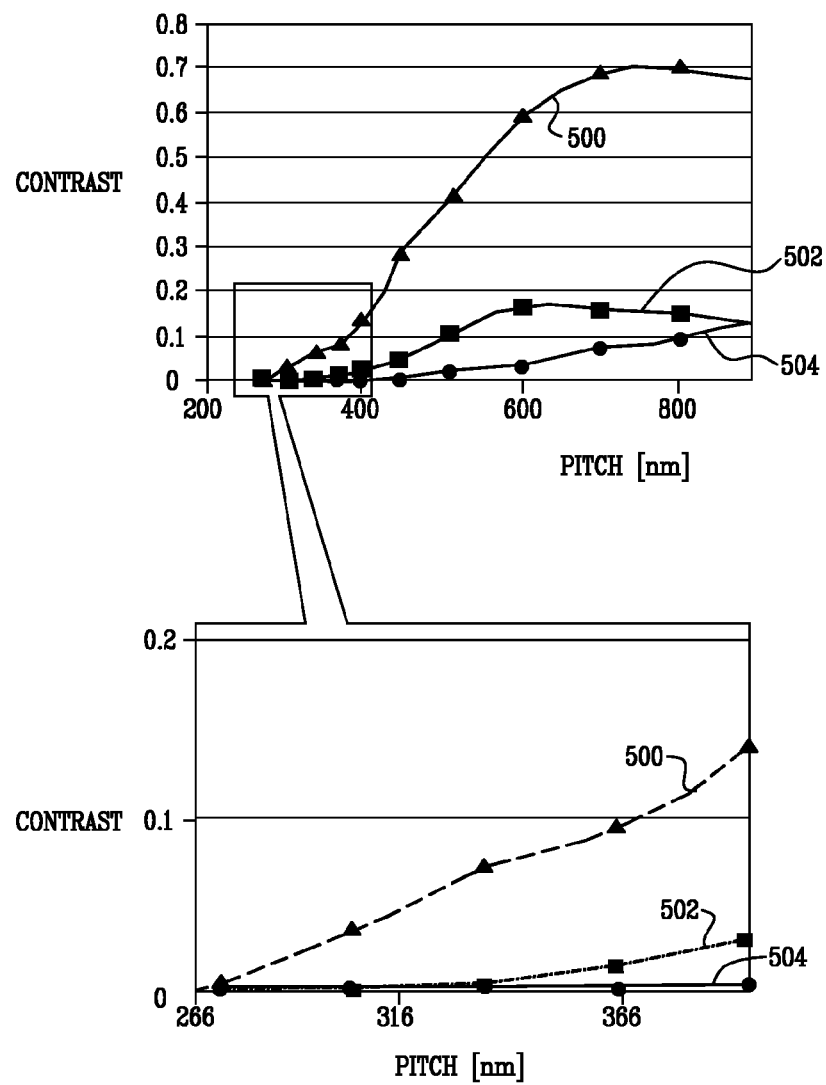
FIG. 7B shows schematic graphs of image contrast vs. pitch for the gratings, according to an embodiment of the present invention.

FIG. 7A is a schematic diagram of gratings imaged by apparatus 20, and FIG. 7B shows schematic graphs of image contrast vs. pitch for the gratings, according to an embodiment of the present invention. The graphs are experimental graphs produced using the disclosed embodiment of apparatus 20 described above, for ten different gratings at location 122. The gratings are parallel polycrystalline silicon lines plated on a doped silicon layer, so that there are parallel doped silicon spaces between the lines. The widths of the lines and the spaces between the lines are substantially equal. The graphs show measured image contrasts for differently pitched sets of lines.

The plated lines have pitches of approximately 272 nm, 300 nm, 335 nm, 370 nm, 400 nm, 450 nm, 500 nm, 600 nm, 700 nm, and 800 nm. A diagram 400 illustrates the smallest pitch grating of 272 nm; a diagram 402 illustrates the largest pitch grating of 800 nm. In FIG. 7B a graph 500 is for apparatus 20 operating with a pump wavelength $\lambda_{pump}$=440 nm and a probe wavelength $\lambda_{probe}$=635 nm simultaneously. Graph 502 is for the apparatus operating only with the pump beam, and graph 504 is for the apparatus operating only with the probe beam. FIG. 7B also shows a lower left section of graphs 500, 502, and 504 on a magnified scale.

Inspection of the graphs demonstrates that the resolution of the combined pump-probe system is significantly greater than either the pump beam system or the probe beam system alone. Thus, graph 500 shows that the combined pump-probe system cuts off at approximately 270 nm, whereas using the probe alone, at a wavelength of 440 nm, the cut off is approximately 350 nm. The inventors measured the cut off for the probe alone, operating at a wavelength of 635 nm, to be approximately 470 nm. The combined pump-probe beam cut-off of approximately 270 nm corresponds with the predicted cut-off of 260 nm given by equations (4) and (5).

The graphs of FIG. 7B are for materials comprising different types of semiconductors. In this case, the pump radiation typically causes changes in the returning probe radiation because of different levels of excess carriers in the different types of semiconductors.

The inventors have found generally similar effects to those illustrated in the graphs of FIG. 7B for sets of parallel metal lines plated on a dielectric or on a semiconductor surface. In the case of metals, the changes in the returning probe radiation are caused by the temperature change induced in the metal by the modulation of the pump radiation, which in turn is a function of the thermal response, i.e., the diffusion time scale, of the metal. The thermal response of the metal depends on the physical dimensions of the metal, for example, a thin parallel metal strip has a different response from a thin metal plane. The thermal response also depends on the specific heat capacity of the metal, the response changing inversely with the specific heat capacity. In addition, the temperature change induced into the metal depends on the modulation frequency of the pump radiation. In general, for a region that includes a metal, to achieve resolutions in a given direction of the region that are comparable to those described above for semiconductors, the modulation frequency is typically higher than the diffusion time scale in the direction, so that there is substantially no diffusion of heat from the pump spot in that direction.

The increased resolution of the effective reduced wavelength $\lambda_{eff}$ may also be applied to improving the resolution of metal features on surface 69 other than those described above. For example, substantially similar improved resolution images may be formed for temperature variations in metals, such as in the example described below with reference to FIG. 8.

Figure 8:
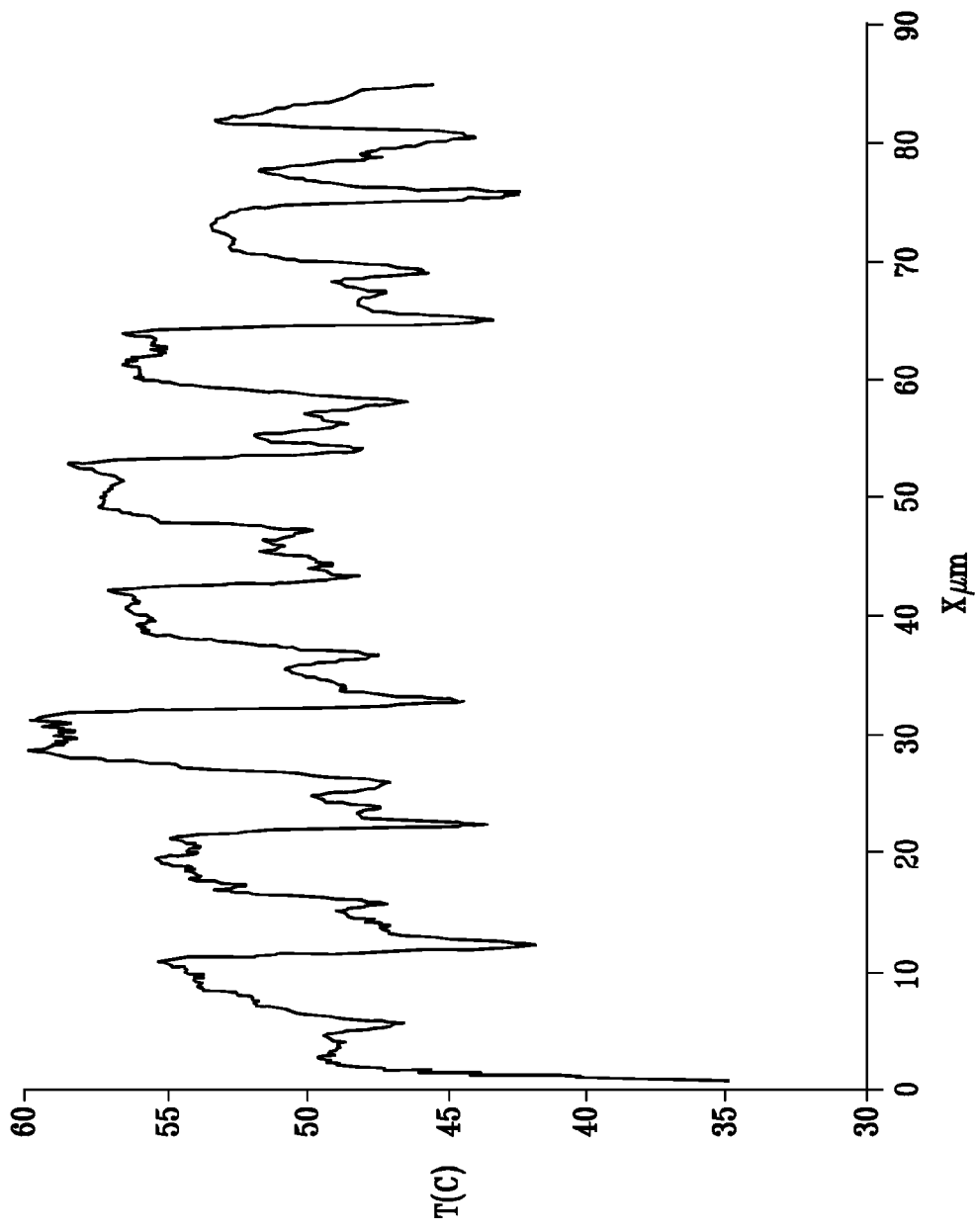
FIG. 8 is a schematic graph of temperature vs. distance, according to an embodiment of the present invention.

FIG. 8 is a schematic graph of temperature vs. distance, according to an embodiment of the present invention. The graph shows the temperature variation, measured by detectors 128 and/or 134 in the disclosed embodiment described above, along a copper line on a silicon substrate. The copper line has periodic width variations along the line, and a thermal current generated by the pump beam flows in the line, causing the temperature of the line to vary. The high temperature sections correspond to narrow sections of the line, the low temperature sections correspond to wide sections of the line. The graph illustrates the variation in temperature as measured at the improved resolution of $\lambda_{eff}$.

Figure 9:
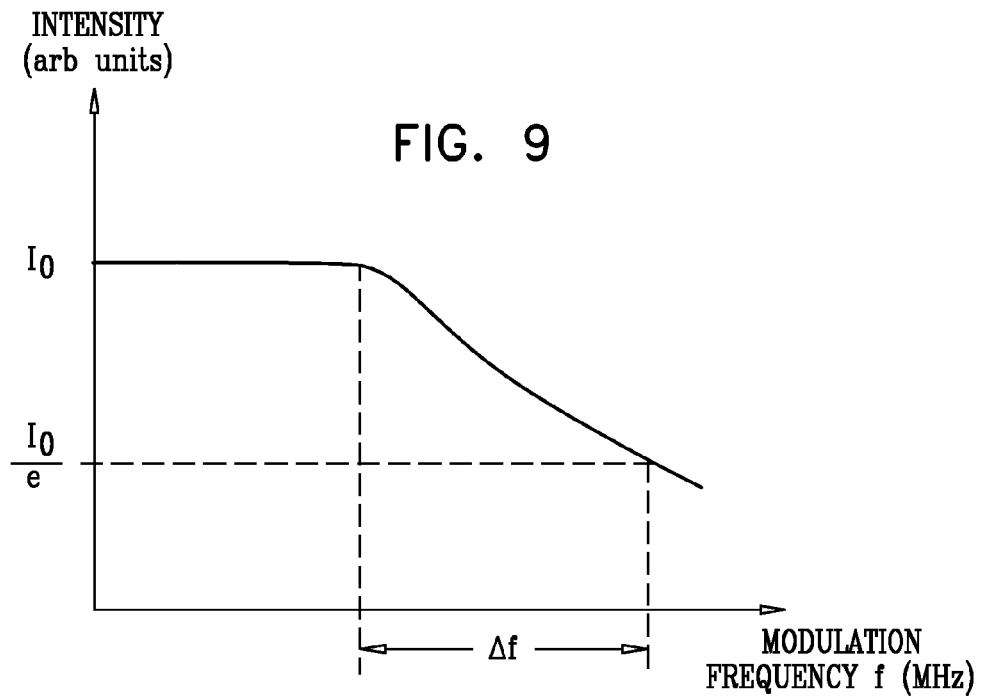
FIG. 9 is a schematic graph of intensity vs. modulation frequency, according to an embodiment of the present invention.

FIG. 9 is a schematic graph of intensity vs. modulation frequency, according to an embodiment of the present invention. The graph gives the intensity determined by detectors 134 and/or 128 as the modulation frequency f is varied, when surface 69 comprises a metal. In the case of a metal, the level of carriers is not a function of the pump beam intensity or wavelength, and is approximately constant. The intensity given by detectors 134/128 mainly varies only according to the temperature of the metal, as is exemplified above by the graph of FIG. 8.

For low frequencies of modulation of the pump beam, the intensity of the returning probe radiation is quasi-steady, since the diffusion of heat from the metal keeps pace with the changes of heat flux due to the modulation of the pump beam. As the modulation frequency increases, the diffusion of heat begins to be unable to follow the changes of heat flux, leading to the intensity of the returning probe beam reducing approximately exponentially, at a rate that is approximately directly proportional to a thermal capacity of the irradiated metal. Thus, the change of modulation frequency $\Delta f$ required to decrease the returning probe beam intensity by a factor of e in the intensity gives a measure of the thermal capacity Q of the metal irradiated, i.e., $$Q \approx k_1 \cdot \Delta f \tag{7}$$

where: $k_1$ is a constant which may be determined by calibration of the apparatus.

Thus, apparatus 20 may be used to measure the thermal capacity Q of the irradiated metal. A thermal capacity measurement can be beneficial since it is closely correlated to the feature geometrical dimensions, such as a thickness of the feature.

Figure 10:
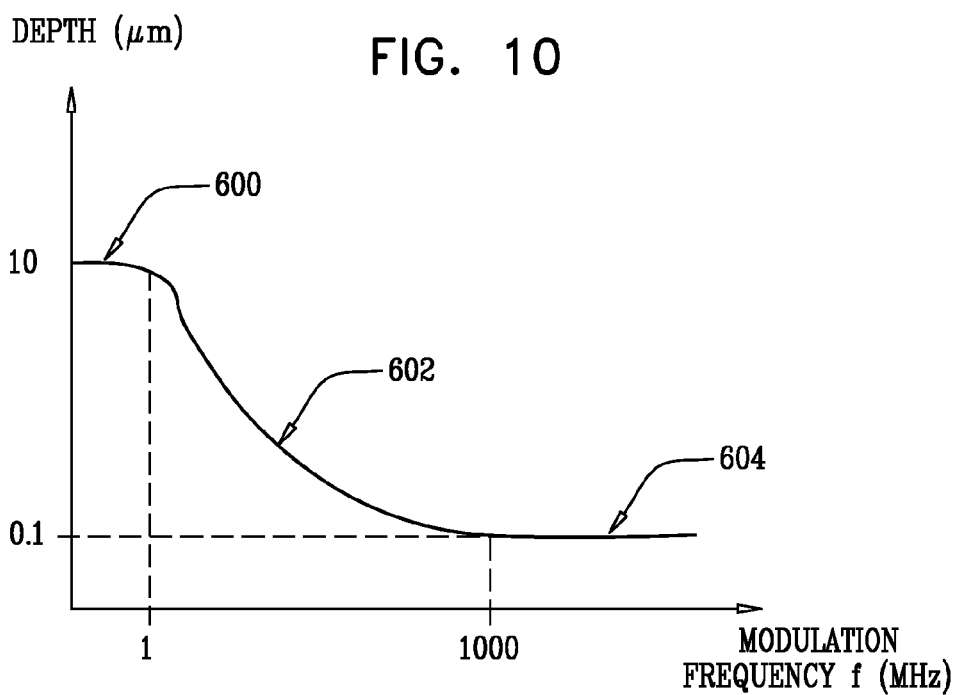
FIG. 10 is a schematic graph of intensity vs. modulation frequency, according to an alternative embodiment of the present invention.

FIG. 10 is a schematic graph of intensity vs. modulation frequency, according to an embodiment of the present invention. The graph gives the intensity determined by detectors 134 and/or 128 as the modulation frequency f is varied, when surface 69 comprises a semiconductor. In the semiconductor, the level of excess carriers is a function of the pump beam intensity and of the pump wavelength. At relatively low frequencies of pump modulation, the excess carriers diffuse from the region of irradiation on surface 69, typically to depths of the order of 10 μm, before the concentration of the carriers effectively becomes zero by a process of recombination. Thus, in a region 600 of the graph, at relatively low pump beam modulation frequencies below of the order of 1 MHz, the depth of the excess carriers is effectively limited by the diffusion depth of the carriers.

At frequencies higher than of the order of 1 GHz, in a region 604 of the graph, the depth of the excess carriers is effectively limited by the penetration depth of the pump beam. The penetration depth of the pump beam depends on the wavelength of the pump beam and is of the order of 0.1 μm for crystalline silicon.

However, in an intermediate region 602 of the graph, at pump beam modulation frequencies between of the order of 1 MHz and of the order of 1 GHz, the effective depth of the excess carriers may be varied by adjusting the pump beam modulation frequency.

In the intermediate region, if the modulation frequency increases, the increased frequency effectively reduces the depth to which the excess carriers penetrate, as illustrated by the graph. In a portion of region 602 an effective depth D of the carriers is approximately inversely proportional to the modulation frequency f, i.e., $$D \approx k_2 \cdot \frac{1}{f} \tag{8}$$

where: $k_2$ is a constant which may be determined by calibration of the apparatus.

Furthermore, a relation between D and f for the whole of region 602 may be determined without undue experimentation. Thus, in a limited range of frequencies, exemplified by region 602 of the graph of FIG. 10, apparatus 20 may be used to adjust an effective depth of the excess carriers generated in an irradiated semiconductor. The adjustment enables an operator of apparatus 20 to inspect a specimen such as wafer 70 at a chosen depth beneath surface 69. The control over the depth is of importance for looking for sub surface defects on the one hand, in a low f regime, and for blocking out a sub layer signal on the other hand, in a high f regime.

Returning to FIG. 1B, operating apparatus 30 in either the first mode or the second mode may provide all the information determined for surface 69, as described above with reference to FIGS. 2-10. In addition, processor 36 may switch between the two modes of apparatus 30 according to the physical responsiveness of the materials under inspection, and use measurements of both modes. The complementary measurements generated by alternating pump and probe lasers can yield more information regarding surface 69 than is available by just operating in one mode.

The complementary measurements may also be beneficial as some materials may have a stronger response to excitation or pumping in the wavelength of source 22 and probing with source 62, as opposed to the opposite case. For example, operating in a first mode that pumps at a wavelength below the energy band gap of a semiconductor in surface 69 may not generate a strong signal from the semiconductor, but may generate a strong signal from another element of the surface. Operating in a second mode that pumps at a wavelength above the energy band gap of the semiconductor typically does generate a strong signal from the semiconductor, but may not generate a strong signal from the other element.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. Apparatus for inspecting a region of a substrate, comprising:
   a first beam generator that generates a first beam at a first wavelength $\lambda 1$;
   a second beam generator that generates a second beam at a second wavelength $\lambda 2$;
   a modulation unit operative in a first mode to modulate an intensity of the first beam at a first frequency while an intensity of the second beam is unmodulated, and in a second mode to modulate the intensity of the second beam at a second frequency while the first beam is unmodulated;

an optical system which is configured to convey the first beam and the second beam to the region; and a detector that receives returning radiation from the region generated in response to the modulation unit operating in the first mode and the second mode, and that forms an image of the region in response to the returning radiation.

2. The apparatus according to claim 1, wherein the first beam follows a first optical path through the optical system and the second beam follows a second optical path through the optical system, and wherein the first and second optical paths have matching optical parameters.

3. A method for inspecting a region of a substrate, comprising:

generating a first beam at a first wavelength $\lambda 1$;

generating a second beam at a second wavelength $\lambda 2$;

modulating the intensity of the first beam at a first frequency in a first mode of operation while an intensity of the second beam is unmodulated, and modulating the intensity of the second beam at a second frequency in a second mode of operation while an intensity of the first beam is unmodulated;

conveying the first beam and the second beam to the region; and receiving returning radiation from the region generated in response to operation in the first mode and operation in the second mode, and forming an image of the region in response to the returning radiation.

4. The method according to claim 3, wherein the first beam follows a first optical path through an optical system and the second beam follows a second optical path through the optical system, and wherein the first and second optical paths have matching, optical parameters.

* * * * *